(12) United States Patent
Green et al.

(10) Patent No.: US 9,759,716 B2
(45) Date of Patent: *Sep. 12, 2017

(54) COMPOSITIONS, APPARATUS AND METHODS FOR MONITORING BIOMARKERS

(71) Applicant: Berkeley Nox Limited, Ballybrit Co. Galway (IE)

(72) Inventors: Natalie Green, Sacramento, CA (US); Juliana Green, Sacramento, CA (US)

(73) Assignee: Berkeley NOX Limited, Ballybrit Co. Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,362

(22) Filed: May 17, 2016

(65) Prior Publication Data

US 2017/0074866 A1 Mar. 16, 2017

Related U.S. Application Data

(63) Continuation of application No. 14/020,065, filed on Sep. 6, 2013, now Pat. No. 9,360,490.

(60) Provisional application No. 61/697,462, filed on Sep. 6, 2012.

(51) Int. Cl.
*G01N 21/75* (2006.01)
*G01N 33/52* (2006.01)
*G01N 33/84* (2006.01)

(52) U.S. Cl.
CPC ........... *G01N 33/526* (2013.01); *G01N 33/84* (2013.01); *G01N 2800/32* (2013.01); *G01N 2800/708* (2013.01); *Y10T 436/177692* (2015.01)

(58) Field of Classification Search
CPC .. G01N 33/526; G01N 33/84; G01N 2800/32; G01N 2800/708
See application file for complete search history.

(56) References Cited

U.S. PATENT DOCUMENTS

| | | | |
|---|---|---|---|
| 3,817,705 | A | 6/1974 | Stein et al. |
| 4,962,025 | A | 10/1990 | Moldowan |
| 2004/0071594 | A1 | 4/2004 | Malone et al. |
| 2012/0083711 | A1 | 4/2012 | Goldstein et al. |
| 2012/0203465 | A1 | 8/2012 | Callewaert et al. |
| 2012/0321724 | A1* | 12/2012 | Bryan ................. A61K 31/195 424/718 |

FOREIGN PATENT DOCUMENTS

GB 2340940 3/2000
WO 02071071 9/2002
(Continued)

OTHER PUBLICATIONS

Blicharz et al. "Use of Colorimetric Test Strips for Monitoring the Effect of Hemodialysis on Salivary Nitrite and Uric Acid in Patients with End-Stage Renal Disease: a Proof of Principle", Clinical Chemistry, 24(9):1473-1480 (2008).
(Continued)

*Primary Examiner* — Dennis M White
(74) *Attorney, Agent, or Firm* — DLA Piper LLP (US)

(57) ABSTRACT

A single device to collect, transfer, and measure salivary nitric oxide analyte and metabolite, nitrite, a biomarker for nitric oxide, as well as, a method to assess the effects of diet and exercise on changing an individual's nitric oxide status and health.

10 Claims, 1 Drawing Sheet

(56) References Cited

FOREIGN PATENT DOCUMENTS

| WO | 2010090810 | 8/2010 |
|----|------------|--------|
| WO | 2011048168 | 4/2011 |
| WO | 2013023217 | 2/2013 |

OTHER PUBLICATIONS

Blicharz et al. "Supplemental Data: Monitoring the effect of hemodialysis on salivary nitrite and uric acid in end-stage renal disease patients using colorimetric test strips: a proof of principle", littp.//www.clinchem.org/content/suppl/2008/09/25/clinchem.2008.105320.DC1/clinchem.2008.105320-1.pdf., 8pp (retrieved Sep. 1, 2013).

Li et al. "Quantitative biomarker assay with microfluidic paper-based analytical devices", Anal Bioanal Chem, 396:495-501 (Oct. 18, 2009).

Klasner et al. "Paper-based microfluidic devices for analysis of clinically relevant analytes present in urine and saliva", Anal Bioanal Chem, 397:1821-1829 (Apr. 28, 2010).

Gubala et al. "Point of Care Diagnostics: Status and Future", Analytical Chemistry, 84:847-515 (2012).

\* cited by examiner

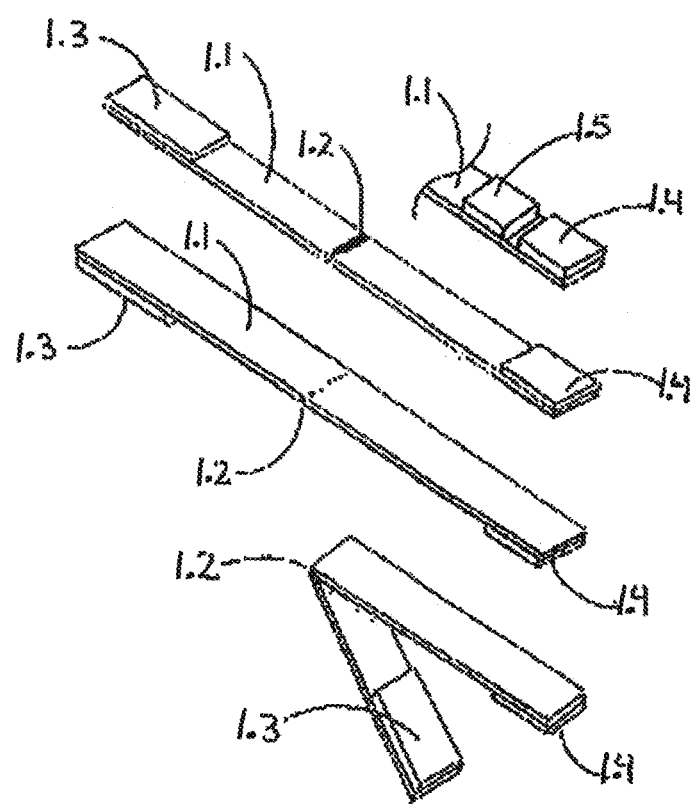

COMPOSITIONS, APPARATUS AND METHODS FOR MONITORING BIOMARKERS

CROSS REFERENCE TO RELATED PATENT APPLICATIONS

The present application is a continuation application of U.S. patent application Ser. No. 14/020,065 filed on Sep. 6, 2013, which claims priority to U.S. Provisional Patent Application Ser. No. 61/697,462 filed on Sep. 6, 2012. The present application is also related to U.S. Provisional Patent Application Ser. No. 61/451,221 filed on Mar. 10, 2011, all of which are incorporated herein in their entireties.

FIELD OF THE INVENTION

The present invention relates to compositions, methods and apparatus for monitoring the status of biomarkers. The present invention is particularly suited for providing information about an organism's physiological, metabolic, or pathological status. In certain embodiments, the present invention comprises an easy to use apparatus for measuring physiological biomarkers such as metabolites, chemicals, hormones, toxins, enzymes, immnunoglobulins, proteins, and nucleic acids, in bodily fluids such as saliva, tears, sweat, urine, and blood. In a particular embodiment, the present invention provides a method and apparatus for monitoring nitric oxide analytes and metabolites in saliva; this information may be utilized as it relates to diets that improve cardiovascular health, i.e., lowering of blood pressure with the ingestion of vegetables that increase salivary nitrite levels, a biomarker for nitric oxide, with a corresponding decrease in blood pressure.

BACKGROUND OF THE INVENTION

While numerous diagnoses and physical assessments require the use of sophisticated equipment and extensive testing by specialists in clinics, a deeper understanding of biomarkers and their significance provides an opportunity to utilize this information in less obtrusive, less expensive, and less burdensome way. Recent technological advances, along with a better comprehension of metabolic, biochemical and physiological processes have enabled individuals to assume greater responsibility for their own wellness, health and physical fitness. Detection of such biomarkers may provide information that can assist individuals in assessing physiological status, and consequently making appropriate adjustments.

Numerous commercial tests are currently available to the general public, and such tests enable consumers to monitor their health in the privacy of their own homes, without the inconvenience or time-consuming activity of travelling to a healthcare or laboratory facility. Examples of such tests include the pregnancy test (biomarker detected is human chorionic gonadotropin (HCG), test media is urine), blood glucose test (biomarker detected is glucose metabolite, test media is blood), cholesterol test (biomarkers detected include HDL, LDL, and triglycerides, test media is blood), and prostate specific antigen (PSA) test (biomarker detected is PSA, test media is blood). The rising popularity of such tests supports the notion that consumers are becoming increasingly proactive about monitoring various aspects of their health, presumably in an effort to prevent illness and improve quality of life.

One particular segment of the population that is keenly attuned to their health and physical status comprises individuals that exercise on a regular basis and athletes. Their goals of maintaining good physical health are frequently coupled with, or closely tied to, maintaining good cardiovascular health.

Along with vascular aging and metabolic disorders, such as obesity, hypertension, and diabetic insulin resistance, prevalent promoters of cardiovascular disease are also on the rise. Although there is an inheritable basis to cardiovascular disease, poor diet and physical inactivity remain the primary drivers. Much of the latest biomedical research supports the need for a daily lifestyle comprising a cardioprotective diet as part of a solution.

Naturally produced nitric oxide is emerging as a critically important cardioprotective and vascular wellness factor. With age, arteries lose their elasticity and ability to make nitric oxide to prevent cardiovascular disease. Scientific evidence suggests that vascular aging may be delayed through the increased production of nitric oxide, thereby, enhancing cardiovascular function. Athletes have already taken advantage of these discoveries by increasing their consumption of leafy greens and beetroots, both of which are rich in nitrate, to elevate nitric oxide levels that increase endurance and performance.

A recent study (Apr. 15, 2013) conducted by researchers from Queen Mary University of London, and published in the American Heart Association Journal, *Hypertension*, provides further support for the importance of nitric oxide and of the blood pressure lowering effects on nitrate-rich vegetables. (Enhanced vasodilator activity of nitrite in hypertension: critical role for erythrocytic xanthine oxidoreductase and translational potential. Ghosh S M et al. Hypertension. 2013 May; 61(5):1091-102. Subjects who drank beetroot juice containing a natural source of inorganic nitrate show an average 10-point decrease in their blood pressure. Sustaining such levels may be critical in maintaining normal blood pressure. The lead author, Dr. Ahluwalia, reported to Medical Xpress: "our hope is that increasing one's intake of vegetables with a high dietary nitrate content, such as green leafy vegetables or beet root, might be a lifestyle approach that one could easily employ to improve cardiovascular health."

A growing number of individuals, especially athletes, are interested in monitoring their nitric oxide status and modifying their whole food diets to optimize cardiovascular fitness. To determine whether an individual has consumed a sufficient quantity of nitric oxide-potent foods such as spinach, arugula, and beets, there is a need for a convenient method and device that is easy to use, and administer. Preferably such a method and device is simple, and inexpensive so that regular monitoring (even multiple times a day) is not burdensome either in the practice of the test or the cost of the test.

As mentioned previously, a number of devices for collecting and testing bodily fluids (i.e., saliva) for the presence of various metabolites exist in the art. In the context of providing a relatively quick and inexpensive sample collecting device and associated testing system, there exist several approaches for collecting a sample fluid, expressing the sample fluid in a test device and performing an assay of the sample. Examples of these types of testing systems include U.S. Pat. Nos. 5,965,453; 6,027,943; 4,895,808; 4,943,522; 6,267,722, 5,393,496, 7,763,433 and 7,507,374.

Prior art devices typically include a sample collector, a container for holding the sample collector and a testing apparatus. One type of sample collector typically includes an absorbent pad for absorbing the target fluid and a holder for holding the sample as the sample is being collected. The sample is then transferred to a sample container or test device by using one of a variety of known approaches including a mechanism for expressing the sample into a sample container (see U.S. Pat. No. 5,268,148) or dipping the sample collector into a test solution (see U.S. Pat. No. 4,895,808) or using a second filter or absorbent pad to transfer the fluid from the collector pad to an intermediate container or test device. Sample collectors may also include a sponge or chemical reagent disposed on a filter strip, which may indicate that an adequate sample is collected (see U.S. Pat. No. 5,393,496).

Strip tests with an absorption pad or chemical reagent test pad are often used in applications for home testing and rapid point of care testing. In some instances, the chemical reagent test pad also serves as the absorption pad.

A major limitation of using the above-mentioned tests for saliva is that since these tests typically incorporate at least one or more chemicals into the test pad/strip, they may not be directly- or safely-inserted into the mouth: in measuring metabolites found in the mouth, the chemical reagent test pad cannot be directly inserted into the mouth, because the chemical reagents can be harmful or toxic. Hence, in the case of saliva, a separated collection system is always necessary and is usually a separate device or apparatus or approach to transfer fluid to the test pad. An example of such a device is the NEO40® or NEOGENIS® test, which actually uses one's hand or finger to transfer the saliva to the test strip, i.e., spit on the finger and transfer spit to chemical test pad. (www.neogenis.com). Inevitably, such a design, where the saliva must first be obtained from the mouth and then transferred (i.e. by a finger) to the test pad, is not only awkward, but can also potentially contaminate results.

Other saliva tests involve a chemical reaction using a lateral flow membrane, that involves an encased test pad (which prevents contact with the mucosa of the mouth) and a wicking pad extension that is inserted into the mouth to collect saliva, which utilizes capillary action to migrate the saliva into the encased device containing the chemical test pad for the reaction to take place. Unfortunately, this is both an expensive (due to the encased device) and timely process, because of the amount of fluid which needs to be collected for the fluid to migrate into the chamber and for the fluid to make contact with the chemical reagents.

Therefore, currently available test strips are limited only to the chemical reaction, hence, the pad must be directly introduced into the test fluid outside of the mouth. Again, in the case of saliva fluid this creates a problem, since it would not be prudent to place the chemical reagent test pad directly into the mouth, as many of the dry test reagents comprise irritants, carcinogenic, or toxic chemicals that may be harmful, hence, the collection of saliva fluid is necessitates a separate device.

What is needed therefore are simple, easy to use devices that enable users to quickly, and accurately measure biomarkers of interest. In particular, what is needed are tests that can be used to detect biomarkers such as metabolites, chemicals, hormones, toxins, enzymes, immunoglobulins, proteins, and nucleic acids, in bodily fluids such as saliva, tears, sweat, urine, and blood. More particularly, a test that may be used directly in the oral cavity for measuring nitric oxide status is desired.

SUMMARY OF THE INVENTION

The present invention is related to methods and devices for the detection of biomarkers in bodily fluids. In one embodiment, the present invention provides for the first time a single device to collect, transfer, and measure saliva nitric oxide analytes, including, but not limited, to nitrite, a precursor and biomarker for nitric oxide, and method to assess cardiovascular wellness and fitness.

Through the detection of saliva analyte and a biomarker of nitric oxide, both a cardioprotective factor in at-risk populations and oxygen sparing factor in athletes, the present invention enables individuals to make real-time adjustments to diets and exercise and other lifestyle changes that impact cardiovascular performance. According to the present invention users are able to rapidly, in a real-time fashion, evaluate their own response to nitric oxide enhancing activities, specifically, vigorous exercise and leafy green-rich diets for cardiovascular function and determine a corrective course by altering exercise and diet to enhance cardiovascular wellness and fitness.

Hallmarks of cardiovascular wellness and athletic fitness through daily exercise and proper diet can be characterized as the ability to maintain normal blood pressure levels or the ability to lower blood pressure, extend time-to-exhaustion during physical activity, and reverse or prevent the elevation of cardiovascular risk factors, including, but not limited to, low density lipoproteins, or elevate cardioprotective factors, such as nitric oxide.

The present invention comprises a single device, two-step method test for both collecting and measuring saliva nitrogen oxides anions, specifically, but not limited to, nitrite, an analyte of or biomarker for nitric oxide, to assess salivary nitric oxide levels at any time, such as before and after physical exercise and meals to assess cardiovascular wellness and athletic fitness. The present invention comprises the use of an elongated test strip, wherein, the test strip contains two or more pads on each end of the strip. The strip contains a scored mark at the midpoint of the strip and in certain embodiments, one end of the strip contains a first absorbent pad, and the opposite end contains a second absorbent pad at the opposite end: the first absorbent pad comprises a fluid collection pad, and the second absorbent pad comprises a test pad. The fluid collection pad is used to absorb saliva, and then by folding along the scored line of strip, the saliva is brought into contact with the test pad. The test pad may contain one or more testing/analyzing zones. In one embodiment, the testing zone comprises dry chemical reagents that indicate presence of nitric oxide in saliva by producing a colorimetric reaction. In certain other embodiments, more than one zone may be included to indicate the presence of other biomarkers. In the embodiment wherein the presence of nitric oxide is determined as a result of color change, the resulting color is compared to a color chart corresponding to concentrations of nitric oxide. The color chart not only indicates how much nitric oxide may be present, it also provides information that enables the user to evaluate cardiovascular wellness and fitness, to evaluate response to exercise and diet for cardiovascular function, or determine a corrective course by altering exercise and diet to enhance vascular wellness and fitness. In certain embodiments, the color chart provides a range that assesses nitric oxide levels starting with "depleted" (nitric oxide poor-diet), then "low", then "threshold" (nitric oxide-rich diet), then "target" and finally "high". As the color intensity increases, the levels of nitric oxide increase.

Through the use of an easy to use saliva test device to collect and measure nitric oxide analytes in saliva fluid, it is an object of the present invention to promote healthy eating habits and promote exercise to prevent cardiovascular disease in an at risk and aging population.

Another object of the present invention is to provide a rapid, inexpensive, self-administered saliva test device and method to collect and measure nitric oxide analytes in saliva fluids to monitor nitric oxide levels in athletes, thereby, providing insight as to anticipated oxygen consumption demands and cellular respirator function.

A further object of the present invention is to provide an easy to use single unit monitoring device that enables consumers to detect biomarkers in bodily fluids.

These and other objects, features and advantages of the present invention will become apparent after a review of the following detailed description of the disclosed embodiments and the appended claims.

BRIEF DESCRIPTION OF THE FIGURE

As shown in FIG. 1., the device is an elongated strip (FIG. 1.1.) that has a scored mark, crease, or partial cut at the midpoint (FIG. 1.2.) to allow the strip to fold upon itself (FIG. 1.; see partially folded strip in drawing), by pressing together with the thumb and forefinger, thereby, transferring saliva collected on an absorption pad (FIG. 1.3.) at one end of the strip to the dry chemical reagent test pad at the other end of the strip (FIG. 1.4.). To detect multiple analytes, saliva fluid is transferred to multiple test reagent pads (FIGS. 1.4 and 1.5; see partial strip in drawing), which each contain dry chemical reagents that specifically react with distinctively different analytes found in the saliva fluid.

DETAILED DESCRIPTION OF THE INVENTION

The present invention may be understood more readily by reference to the following detailed description of the specific embodiments included herein. Reference is made to the accompanying drawings, which form a part hereof, and in which is shown, by way of illustration, various embodiments of the present disclosure. Although the present invention has been described with reference to specific details of certain embodiments thereof, it is not intended that such details should be regarded as limitations upon the scope of the invention.

The entire text of the references mentioned herein are hereby incorporated in their entireties by reference including U.S. Provisional Patent Application Ser. No. 61/697,462 filed on Sep. 6, 2012 and U.S. Provisional Patent Application Ser. No. 61/451,221 filed on Mar. 10, 2011.

From detecting cancer, to monitoring blood glucose levels and detecting HCG in order to confirm pregnancy, biomarkers have rapidly gained importance as indicators of physiological health. With advances in the identification of specific biomarkers and their role in indicating various physiological or pathological states, there is heightened interest in incorporating the detection of such biomarkers into commercially available, over-the-counter test kits in order to provide consumers with a convenient and cost-effective option for monitoring and maintaining their physical well being. Such tests have the potential to analyze bodily fluids, including but not limited to, saliva, sputum, tears, sweat, mucus, serum, semen, urine and blood, to detect biomarkers, including but not limited to, analytes, metabolites, chemicals, hormones, toxins, enzymes, immunoglobulins, proteins, and nucleic acids.

The confluence of increasing health care costs together with increasing knowledge concerning the causality of many health conditions, mandates a prudent approach to monitoring factors that cause illness or lead to poor physiological status. The use of information concerning biomarkers may be incorporated into tests that allow individuals to follow their health and well-being and to make adjustments to their lifestyle (i.e. diet and exercise) as necessary. Just as glucose monitors have been instrumental in enabling diabetic patients to monitor blood sugar levels and thereby manage their healthcare, there exists tremendous potential and need for tests that utilize other biomarkers to better maintain health. Biomarkers can be useful in predicting risk, screening, diagnosis, scaling severity, monitoring progress, predicting response to therapy, determining prognosis and understanding disease mechanism.

The present invention comprises the use of biomarker information in easy to use tests in order to provide individuals with useful information about their health. The tests included herein involve the analysis of bodily fluids to detect a variety of biomarkers. Body fluids that may be analyzed herein, include but are not limited to, saliva, sputum, tears, sweat, mucus, serum, semen, urine and blood.

The table below provides a representative listing of some biomarkers that may be found in certain bodily fluids:

| Bodily Fluid | Biomarkers |
| --- | --- |
| Saliva | nitric oxide analytes and metabolites, heavy metals (e.g., lead), hormones (e.g., cortisol, dehydroxyepiandrosterone (DHEA)), toxins and their metabolites (e.g., cotinine), enzymes (e.g., lysozyme, α-amylase), immunoglobulins (e.g., IgA), other proteins (e.g., eosinophil cationic protein), DNA |
| Sputum | Sputum eosinophils, leukotriene B4, aberrant gene methylation (p16 and/or $O^6$-methylguanine-DNA methyltransferase promoters), mir-21 expression |
| Tears | EGF, lysozyme, lactoferin, cytokines, INFgamma, TNFalpha, eotaxin, adhesion molecules (ICAM-1, selectin etc.) |
| Sweat | cytokines, neuropeptides, substance P, and calcitonin-gene-related peptide, vasoactive intestinal peptide |
| Mucus | mucin, cytokines, growth factors |
| Serum and blood | tumor markers, growth factors, proteins, immunoglobulins, enzymes, enzyme inhibitors, antigens |
| Semen | proteolytic enzymes, citric acid, acid phosphatase and lipids PSA |
| Urine | metabolites, sugars, Urinary carcinogen metabolite, trans,trans-muconic acid (tt-MA) and S-phenylmercapturic acid (metabolites of benzene), 1- and 2-naphthol, hydroxyphenanthrenes and phenanthrene dihydrodiols, 1-hydroxypyrene (1-HOP), metabolites of benzo[a]pyrene, aromatic amines and heterocyclic aromatic amines, N-nitrosoproline, 4-(methylnitrosamino)-1-(3-pyridyl)-1-butanol and its glucuronides (NNAL and NNAL-Gluc), 8-oxodeoxyguanosine, thioethers, mercapturic acids, and alkyladenines |

The number one leading cause of death in the world according to the World Health Organization is heart disease. In 2011 approximately 7 million people died from some form of ischemic heart disease, and 6.2 million people died from stroke. In the United States, according to the Center for Disease Control, about 600,000 people die of heart disease every year, amounting to 1 in every 4 deaths. Heart disease is the leading cause of death for both men and women, and coronary heart disease is the most common type of heart disease, killing more than 385,000 people annually. It is estimated that coronary heart disease alone costs the United States $108.9 billion each year. (This total includes the cost of health care services, medications, and lost productivity.) Accordingly it is not surprising that there continues to be increasing emphasis on improving and maintaining good cardiovascular health.

In 1998, the Nobel Prize for medicine was awarded to Robert F. Furchgott, Louis J. Ignarro and Ferid Murad for discovering the importance of nitric oxide in the cardiovascular system. These scientists demonstrated that nitric oxide, is a short-lived, endogenously produced gas that acts as a signaling molecule in the body. Signal transmission by a gas, produced by one cell, which penetrates membranes and regulates the function of other cells was recognized for the first time as an entirely new principle for signaling in the human organism. Related research proved the crucial role that nitric oxide plays in such fundamental biological processes as regulation of blood pressure, functioning and malfunctioning of the immune system, and activation of mechanisms in the central nervous system affecting everything from gastric motility to memory to behavior.

Additional research has shown that elevated levels of nitric oxide have numerous beneficial effects including, but not limited to, increasing performance and endurance, as well as improving cardiovascular health and protecting blood vessels from vascular aging. Scientists have further demonstrated that daily consumption of leafy greens, such as spinach, arugula, beetroot, among other nitric oxide-potent vegetables and fruits, is the safest and healthiest way to elevate natural nitric oxide levels. Indeed the National Institutes of Health (NIH) specifically recommends the DASH diet "NIH Dietary Approach to Stop Hypertension" diet that requires 4-5 daily servings of raw leafy vegetables. A similar diet increasingly recommended by physicians is the Mediterranean diet that is also loaded with leafy greens that are cardioprotective by supplying the natural precursor to nitric oxide that our body makes. Olympians, world class runners, swimmers, and cyclists have found that nitric oxide rich vegetables and vegetable-fruit juices concentrated with 'nitric oxide potent' beetroot prolongs the time-to-exhaustion for elite athletes and also lowers the need for oxygen during intensive training.

The present invention is based upon the discovery that nitric oxide is a cardioprotective and an oxygen sparing factor. It is derived from an exogenous or dietary source and endogenous or enzymatic source in our body. The exogenous source is derived from the consumption of leafy green vegetables that are rich in nitrate, which is serially reduced to nitrite and then to nitric oxide. The endogenous source is generated by nitric oxide synthase, an enzyme that utilizes L-arginine, to make nitric oxide. Nitric oxide synthase activity is increased by exercise. Therefore, the consumption of leafy greens and exercise—which both contribute to cardiovascular wellness and fitness—increase the levels of nitric oxide.

Nitrite is a both a precursor of nitric oxide and a biomarker of nitric oxide and saliva nitrite is a surrogate marker for total body nitric oxide levels. Typically, serum blood nitrite is an accepted marker for nitric oxide; however, the collection of blood repeatedly throughout the day is not logistically possible, and neither is subsequent monitoring nitric oxide levels and making the necessary adjustments to elevate nitric oxide levels in order to ensure vascular wellness.

Although substantial evidence has been provided to support the contention that saliva nitrite is a biomarker for nitric oxide, a simple test and method has not yet been developed to monitor nitric oxide levels throughout the day enabling necessary lifestyle adjustments. The present invention allows rapid, non-invasive self administrated testing for nitric oxide through a single device and process to collect, transfer, and measure without the use of other instruments or fingers to transfer fluid.

Recognizing the importance of nitric oxide, its role in promoting good cardiovascular health and the correlation of nitric oxide production with the consumption of specific foods, the inventors herein have developed a unique testing apparatus and method that enables users to quickly and efficiently monitor their nitric oxide status. The invention comprises a saliva test device and method that is useful to assess vascular wellness and fitness. The invention is a single device, three-step method for collecting, transferring, and measuring saliva fluid analytes, specifically for, but not limited to, nitrogen oxide anions, nitrite, an analyte of and biomarker for nitric oxide. The invention may be practiced to assess salivary nitric oxide after exercise, which promotes the synthesis of endogenous nitric oxide, and consumption of nitrate-rich meals, a source of nitrate which is reduced to nitric oxide. The invention is uniquely useful in evaluating a response to exercise and/or nitrate-rich diets for vascular function and determining a corrective course by altering exercise and/or diet to enhance vascular wellness and fitness.

The present invention overcomes the limitations of prior art devices and methods that relied on the collection of saliva fluid via a separate container in which the test pad was inserted. Other prior art devices relied on the collection of saliva by lateral flow membrane and through capillary action wherein the saliva analytes would migrate into a closed chamber for analysis. Still other prior art devices required the physical collecting of saliva fluid and then transferring it by one's own finger to the test pad. The present invention overcomes the limitations of such devices by enabling direct insertion of the test into the oral cavity.

Unlike any previous invention, publication or product, thus far, the present invention provides a single apparatus or method to collect, transfer, and measure saliva analytes in a single multiple test pad strip in particular, for nitric oxide analytes and more specifically for the assessment of vascular wellness as defined herein. In further contrast to previous inventions, publications, or products the present invention provides a test strip to measure nitric oxide analytes in a unique fashion allowing the information to be used to assess vascular wellness and fitness in context of physical exercise or diet.

The present invention, also known as the BERKELEY TEST®, not only monitors nitric oxide status, it also provides an instant readout such that the user can make informed decisions, in real-time, about maintaining a level sufficient to promote vascular wellness. The BERKELEY TEST® enables users such as athletes who need a sensitive, easy to use, and affordable test that can be used 3-4 times daily to make dietary adjustments as needed to maintain optimal levels of nitric oxide.

The present invention comprises a device for detecting the presence of a biomarker in a bodily fluid wherein the device comprises a single unit for collecting the bodily fluid, analyzing the contents of the bodily fluid and correlating the analysis with physiological status. In certain embodiments, bodily fluid comprises saliva and the biomarker comprises nitric oxide, saliva-derived nitric oxide analytes or saliva-derived nitric oxide metabolites.

The present invention generally comprises a single unit comprising an elongated strip, wherein the strip contains a scored mark (or crease) at the midpoint of the strip and wherein the strip contains an absorbent pad at each end. The scored mark enables the strip to be folded easily, thereby, allowing pads at each end of the strip to make contact. The strip contains a first absorbent pad at one end and a second absorbent pad at the opposite end: the first absorbent pad comprises a fluid collection pad, and the second absorbent pad comprises a test pad. The fluid collection pad may comprise a wicking pad, membrane, paper, resin, sponge, immunoabsorbent pad, ionic or other suitable platform that absorbs saliva analytes to be transfer to the test reagent pad, known to those skilled in the art. The test pad enables dry reagent detection chemistry comprising components modified from the Griess diazotization reaction, comprising mixture of naphthylenediamine-dihydrochloride, and sulphanilamide in acidic solution or para-arsanilic acid; and other reactive components known to those skilled in the art. In certain embodiments, the test pad comprises more than one testing zone so that the fluid may be analyzed for more than one biomarker.

In one embodiment the bodily fluid to be tested is saliva. In this embodiment, at one end of the strip, fluid collection pad collects the saliva when inserted into the mouth with absorption pad down or in contact with tongue. In some embodiments, this portion of the test strip may optionally include an identifying marking on the strip such that the user can easily identify it as the portion that is to be inserted into the mouth. After absorption of saliva, the strip is removed from the mouth and folded along the scored line or crease to allow the absorption pad to make contact with the test pad, resulting in the transfer of saliva from the absorption pad to the test pad. The test pad, which is not inserted in the mouth, contains dry chemical reagents which contains components modified from the Griess reaction, either naphthylenediamine-HCL and sulphanilamide or para-arsanilic acid, which display a color product upon contact with saliva fluids containing nitric oxide analyte, nitrite; the color product intensity correlates with a concentration of the saliva nitric oxide analyte, nitrite. The Griess reaction and reagents used to detect and measure nitrite is well known to someone skilled in the art. A color scale is provided for the user so that a correlation can be made to designate physiological nitric oxide status. In certain embodiments, the color chart provides a range that assesses nitric oxide levels starting with "depleted" (nitric oxide poor-diet), then "low", then "threshold" (nitric oxide-rich diet), then "target" and finally "high". As the color intensity increases, the levels of nitric oxide increase.

The unique design of this strip enables easy collection of the test fluid, without requiring an additional vessel, or direct use of fingers to collect or distribute the fluid. In certain embodiments, the absorption pad (fluid collection pad), located on the same side, but opposite end of the elongated strip from that of the test pad, is inserted into the mouth, (under the tongue or sublingually) for a certain period of time within the range of 2-60 seconds, 3-20 seconds or 3-10, most preferably 3-5 seconds, to absorb saliva; the strip is then folded with the thumb and forefinger so that the absorption pad and test reagent pad make contact for 2-60 seconds, 3-20 seconds most preferably 3-5 seconds. Upon release and separation of the absorption pad from the test pad, a colorimetric reaction, based on the chemical detection reagents used, will take place within 45-60 seconds on the test reagent pad resulting in a color intensity and hue that correlates with a physiological concentration of the nitric oxide analyte.

Once the bodily fluid, i.e. the saliva is applied to the test pad for a predetermined amount of time and reaction is allowed to take place therein, the results manifest as a color change. Typically, the original color of the test pad is white, following the chemical reaction between the test fluid and the reagents in the test pad, the color of the test pad changes from white to another color. The resulting color is "matched" with a color scale and wherever the color falls within the scale, a representative physiological nitric oxide content is evaluated. In essence, color intensity on the test pad is compared to a color chart corresponding to physiological concentrations of the nitric oxide analyte which is useful in evaluating response to nitric oxide-inducing exercise and nitric oxide-rich diets for cardiovascular function and determining a corrective course by altering exercise and diet to enhance vascular wellness and fitness. In addition, a reading of physiological nitric oxide levels enables the assessment of vascular wellness and fitness comprising the ability to maintain a normal blood pressure range, lower blood pressure, extend time-to-exhaustion, reduce the need for oxygen consumption, improve cellular respiration and/or mitochrondial efficiency through a combination of daily physical exercise, including anaerobic training, aerobic training, and/or a diet consisting of leafy green vegetables, such as a Mediterranean diet, DASH (Dietary Approach to Stop Hypertension) diet. As used herein, the phrase "Mediterranean diet" comprises a heart-healthy eating plan that emphasizes fruits, vegetables, whole grains, beans, nuts and seeds, and healthy fats. As used herein, the phrase "DASH diet" comprises an eating plan that is low in saturated fat, cholesterol, and total fat, emphasizes fruits, vegetables, fat-free or low-fat milk and milk products; includes whole grain products, fish, poultry, nuts, the plan comprises reduced in lean red meat, sweets, added sugars, and sugar-containing beverages compared to the typical American diet, in addition, the plan is rich in potassium, magnesium, and calcium, as well as protein and fiber. Both diet are based on the cardioprotective effects of leafy greens, which are now believed to be mediated, in part, by the serial reduction and bioconversion of nitrate to nitric oxide in the body of which nitrite; nitrite an intermediate of this pathway as well as precursor and byproduct of nitric oxide, is chemically reduced in the mouth from the release nitrate by the salivary gland, which is an obligatory step to the pathway.

Alternative embodiments optionally provide in addition to a nitric oxide status detection pad, multiple, separate test pads, each containing dry chemical reagents responsive to different concentration of nitric oxide analyte attached to the strip, thereby, increasing the sensitivity; here, the absorption pad is enlarged to cover multiple, separate pads. Aside from nitrite, other biomarkers also included in the separate pads The device of the present invention measures for saliva-derived nitric oxide analytes, which includes, primarily, nitrite anion, and secondarily, other nitrogen oxides anion, including but not limited to, nitrogen dioxide, nitrate, nitric oxide. Alternative versions of the device of the present invention comprise, in addition to a nitrite detection pad, multiple, separate test pads, each containing dry chemical reagents responsive to different nitric oxide analytes are attached to the strip, thereby, indicating concentrations of multiple nitrogen oxide analytes; here, the absorption pad is enlarged to cover multiple, separate pads. The present invention comprises a test pad capable of detecting a concentration range of the nitric oxide analyte from 25 to >400 umol/L nitrite with visibly distinct colorimetric sub-ranges corresponding to (umol/L, ppm, mg/L), specifically, but not limited to: 0 to 25, 25 to 100, 100 to 200, 200 to 350, and greater than 400 umol/L nitrite. Still additional embodiments comprise one or more test pads capable of detecting biomarkers in saliva other than nitric oxide analytes.

The present invention is particularly desirable as it may be used to gauge the benefit and impact of adding nitrate-rich beetroot juice, a recognized natural power food, to the diet of competitive runners. Inorganic nitrate from vegetables, such as beetroots, is converted to nitric oxide in the body delivering a boost to both endurance and performance. Several times each day, the runners placed the present invention (BERKELEY TEST® strip) in their mouths measuring their nitric oxide levels. If the reading was low, more beetroot juice could be added to the diet. For the first time, the concept of monitoring, visualizing, and tracking personal nitric oxide levels has been expanded to include all natural food sources of nitric oxide, so that anybody, not just an athlete, can enjoy the same real-time feedback as they work to optimize their diet for maximum cardiovascular health and wellness.

The following specific examples will illustrate the invention as it applies to the methods of detecting and monitoring biomarkers in bodily fluids. It will be appreciated that other examples, including minor variations in procedures will be apparent to those skilled in the art, and that the invention is not limited to these specific illustrated Examples.

EXAMPLES

Example 1

Monitoring Saliva Nitric Oxide Analyte Using the BERKELEY TEST® Strips Resulted in an Increase Leafy Green Consumption The objective of this survey was to assess whether knowing saliva nitric oxide levels increased leafy green consumption. The study subjects were told that leafy greens, such as spinach and arugula, are nitrate rich foods that the body converts to nitric oxide, a cardioprotective factor. They were asked to use the BERKELEY TEST® strips to measure nitric oxide levels before and two hours after consumption of their meals. Summary observation: 6 of 7 individuals who followed their saliva nitric oxide levels before and after their typical meal, increased their servings of leafy greens by a factor of 2 to 3 per days, which is above their typical 1-2 day. The subjects' levels in the morning were typically less than approximately 25 umol/L and two hours post-meal, their levels were around 200-400umol/L. This simple survey suggested that by knowing that a cardioprotective factor can be elevated with specific foods, which could be visualized by a saliva test, the vast majority of subjects increased their frequency. The subjects also reported that the amount of type of food was influenced as well.

| Leafy green consumption (servings/day) | 0 | 1 | 2 | 3 | 4 |
|---|---|---|---|---|---|
| Before using Berkeley Test (# individuals) | 5 | 1 | 0 | 0 | 0 |
| When using Berkeley Test (# individuals) | 0 | 0 | 4 | 1 | 1 |

Example 2

Monitoring Saliva Nitric Oxide Analyte Before and Two Hours after Cardioproteclive Diets in Context of Systolic BP The objective of this survey was to assess whether saliva nitric oxide status correlated with systolic blood pressure (SBP) 2 hours after consuming a meal enriched with leafy green and beetroot that increased salivary levels above 400 uM within 2-3 hours. The subjects evaluated over a 2-3 hour period, were relatively healthy, non-medicated and prehypertensive (125-130 mmHg). Summary observation: Individuals who exhibited an increase in saliva nitric oxide levels above 400 umol/L 2 hours after the consumption of a nitrate-rich meal consistently showed a 2-4 mmHg reduction in SBP.

| Changes in Systolic Blood Pressure (mmHg) | >+2 | 0 | -2 | -4 | <-8 |
|---|---|---|---|---|---|
| Saliva Nitric Oxide status @ <20 umol/L | 2 | 2 | 1 | 0 | 0 |
| Saliva Nitric Oxide status @ ≥400 umol/L | 0 | 1 | 1 | 2 | 1 |

Having described the invention with reference to a particular device and method for collecting, transferring, and measuring NO analytes in saliva through a rapid, self-administered fashion, both changed behavior to improve cardiovascular fitness and correlated with a reduction of SBP among mildly pre-hypertensives, it will be apparent to those of skill in the art that it is not intended that the invention be limited by such illustrative embodiments, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in which is effective to meet the objectives there intended, unless the context specifically indicates to the contrary. This invention is the first report to demonstrate that a single and stand alone device to rapidly and inexpensively collect, transfer, and measure a nitric oxide analyte results in lifestyle changes that improves cardiovascular health. The uniqueness of the invention is reflected in the simplicity and easy of use of the device and method that allows self-monitoring of cardiovascular fitness in context of diet and exercise.

Example 3

Monitoring Saliva Nitric Oxide Analyte Using BERKELEY TEST® Strips Resulted in an Increase in Exercise Frequency The objective of this initial survey was to assess whether knowing saliva nitric oxide levels before and after exercise influenced the frequency of exercise. Summary observation: Individuals who followed their saliva nitric oxide levels before and after exercise, increased the frequency and in many instances the duration and intensity of their exercise routines. It was not uncommon to find relatively healthy, active individuals add 1 to 2 additional days per week of intense exercise when salivary nitric oxide levels increase post-exercise. Assuming pre-exercise levels were <20 umol/L (hence, this group either fasted or did not include nitrate rich foods into their diet for the past 12 hours), post-exercise level increased by a factor of 1.5. Diet, and exercise duration and intensity, as well as, physical condition of the individual dramatically influenced pre- and post-exercise levels. A clear trend to increase the frequency, duration, and intensity of exercise was evident among individuals knowing that a cardioprotective factor, such as nitric oxide, is naturally elevated with exercise; assessing salivary nitric oxide status with Berkeley Test® was found to be an effective compliance tool to increase physical activity.

What is claimed is:
1. A method for increasing dietary intake of nitrate rich foods comprising the use of a device for the detection of the presence of nitric oxide in saliva,
   wherein the device comprises a single unit for collecting the saliva and analyzing the contents of the saliva, wherein the single unit comprises an elongated strip, wherein the strip contains a scored mark at the midpoint of the strip and wherein the strip contains a first absorbent pad at one end and a second absorbent pad at the opposite end, wherein the first absorbent pad comprises a fluid collection pad, and wherein the second absorbent pad comprises a test pad, wherein the test pad enables dry reagent detection chemistry comprising components modified from the Griess diazotization reaction, comprising mixture of N-naphthylenediamine-dihydrochloride and sulphanilamide, or N-(naphthyl)ethylenediammonium-dihydrochloride and sulphanilamide, or para-arsanilic acid N-ethylenediamine tetrahydroquinoline, or para-arsanilic acid N-(1-naphthyl)ethylenediamine dihydrochoride;

wherein the fluid collection pad is inserted into the mouth for a first predetermined period of time to absorb saliva, wherein the device is then folded so that the fluid collection pad and test pad make contact for a second predetermined period of time, wherein the contact between the fluid collection pad and test pad results in a color change on the test pad following a third predetermined period, wherein the color change is compared to a color scale and wherever the color falls within the scale, a representative physiological nitric oxide content is evaluated; and wherein the test pad provides a concentration range of the nitric oxide analyte, nitrite, ranging from 12 to >400 µmol /L with visibly distinct color ranges corresponding to 0 to 25, 25 to 100, 100 to 200, 200 to 350, or greater than 400 µmol /L.

2. The method of claim 1, wherein the nitrate rich foods contain high levels of cardioprotective and cardio-enhancing factors.

3. The method of claim 2, wherein the nitrate rich foods comprise leafy greens, spinach and arugula.

4. The method of claim 2, wherein the nitrate rich food comprises beetroots, beetroot juice, and beetroot powder.

5. The method of claim 1, wherein the increased dietary intake of nitrate rich foods results in improved cardiovascular health.

6. The method of claim 1, wherein the fluid collection pad comprises a wicking pad, membrane, paper, resin, sponge, immunoabsorbent pad, ionic, or other suitable platform that absorbs saliva analytes to be transferred to the test reagent pad.

7. The method of claim 1, wherein the representative physiological nitric oxide content is utilized to enable the assessment of vascular wellness and fitness.

8. The method of claim 7, wherein vascular wellness and fitness comprises the ability to maintain a normal blood pressure range, lower blood pressure, extend time-to-exhaustion, reduce the need for oxygen consumption, improve cellular respiration, or mitochondrial efficiency.

9. The method of claim 1, wherein the representative physiological nitric oxide content is utilized to enable modification of nitric oxide levels comprising daily physical exercise, anaerobic training, aerobic training, consuming a diet consisting of leafy green vegetables and other nitrate-rich vegetables, fruit, whole foods supplement intended to increase nitric oxide levels, consuming a Mediterranean diet, or consuming a DASH diet.

10. The method of claim 1, wherein the first and second predetermined period of time are about 10 seconds; and wherein the third predetermined period of time is about 10-45 seconds.

* * * * *